United States Patent
Kempe

(10) Patent No.: US 6,734,297 B2
(45) Date of Patent: May 11, 2004

(54) OLIGONUCLEOTIDE LABELING REAGENTS

(75) Inventor: Tomas Kempe, Washington, DC (US)

(73) Assignee: Barrskogen, Inc., Washington, DC (US)

( * ) Notice: Subject to any disclaimer, the term of this patent is extended or adjusted under 35 U.S.C. 154(b) by 0 days.

(21) Appl. No.: 10/341,629

(22) Filed: Jan. 14, 2003

(65) Prior Publication Data

US 2003/0109032 A1 Jun. 12, 2003

Related U.S. Application Data

(63) Continuation of application No. 09/874,161, filed on Jun. 4, 2001, now Pat. No. 6,534,646.

(51) Int. Cl.$^7$ .................. C07H 21/00; C07H 21/02; C07H 21/04; C12Q 1/68; C08F 2/00
(52) U.S. Cl. .................. 536/25.3; 536/25.32; 536/23.1; 435/6; 501/33; 526/72; 526/336
(58) Field of Search .................. 536/23.1, 25.3, 536/25.32; 435/6; 501/33; 526/72, 336

(56) References Cited

U.S. PATENT DOCUMENTS

| | | | |
|---|---|---|---|
| 4,659,774 A | 4/1987 | Webb et al. | 525/54 |
| 4,910,300 A | 3/1990 | Urdea et al. | 536/26 |
| 5,093,232 A | 3/1992 | Urdea et al. | 435/6 |
| 5,118,605 A | 6/1992 | Urdea | 435/6 |
| 5,141,813 A | 8/1992 | Nelson | 428/402 |
| 5,380,833 A | 1/1995 | Urdea | 536/22 |
| 5,451,463 A | 9/1995 | Nelson et al. | 428/402 |
| 5,656,741 A | 8/1997 | Chow et al. | 536/25 |
| 5,717,083 A | 2/1998 | Cook et al. | 536/23 |
| 5,723,591 A | 3/1998 | Livak et al. | 536/22.1 |
| 6,248,877 B1 | 6/2001 | Bonner et al. | 536/25 |
| 6,255,476 B1 | 7/2001 | Vinayak et al. | 536/25.32 |

OTHER PUBLICATIONS

Nelson et al., "A new and versatile reagent for acorporating multiple primary aliphatic amines into synthetic oligonucleotides", Nucleic Acids Research, vol. 17, No. 18, pp. 7179–7185 (1989).

Zuckermann et al, "Efficient methods for attachment of thiol specific probes to the 3'–ends of synthetic oligodeoxyribonucleotides", Nucleic Acids Research, vol. 15, No. 13, pp. 5305–5321 (1987).

Misiura et al, "Biotinyl and phosphotyrosinyl phosphoramidite derivatives useful in the incorporation of multiple reporter groups . . . ", Nucleic Acid Research, vol. 18, No. 15, pp. 4345–4354 (1990).

*Primary Examiner*—Jezia Riley
(74) *Attorney, Agent, or Firm*—Fredrikson & Byron, P.A.

(57) ABSTRACT

A labeling reagent for use in oligonucleotide ("oligo") synthesis, as well as a method of preparing such a labeling reagent, a method of using such a reagent for synthesizing a labeled oligonucleotide, and an oligonucleotide prepared using such a reagent. The reagent can be used to label either the 3' or 5' termini of a synthesized oligo, and/or for one or more positions along the oligo. The labeling reagent can be prepared by a reaction scheme that involves the initial preparation of hydroxyacids, tritylated hydroxyacids and coupling of such derivatives to diamine, wherein the amine function serves at an attachment point for labels and the hydroxyl groups can either be used to immoblize the molecules to support or can be converted to provide a phosphorylating reagent.

14 Claims, No Drawings

OLIGONUCLEOTIDE LABELING REAGENTS

CROSS REFERENCE TO RELATED APPLICATIONS

The present application is a continuation of U.S. patent application filed Jun. 4, 2001 and assigned Ser. No. 09/874,161, now U.S. Pat. No. 6,534,646, the entire disclosure of which is incorporated herein by reference.

TECHNICAL FIELD

This invention relates to methods and reagents for oligonucleotide synthesis, including for instance, reagents used to prepare labeled oligonucleotides.

BACKGROUND OF THE INVENTION

A variety of approaches exist, and in turn, a variety of reagents are available, for use in incorporating labeled molecules in synthetic oligonucleotides. For instance, the following sections repeat or paraphrase certain relevant portions of Nelson U.S. Pat. No. 5,451,463 in this regard, which itself is referred to in greater detail below.

"Methods to covalently attach labels and reporter molecules to oligonucleotides have provided valuable tools in the field of molecular biology and gene probe diagnostics. Recent advances in the preparation of non-isotopic gene probes, DNA sequencing (Connell, C. et al. [1987] Biotechniques 5:342–346; Kaiser, R., S. Mackellar, R. Vinayak, J. Sanders, R. Saavedra, L. Hood [1989] Nucleic Acids Res. 17:6087–6102), electron microscopy (Sproat, B. S., B. Beijer, P. Rider [1987] Nucleic Acids Res. 15:6181–6196), and X-ray crystallography (Sproat et al. [1987] Nucleic Acids Res. 15:4837–4848) have provided the impetus for the development and improvement of such methods. Similarly, new and emerging applications employing the polymerase chain reaction (PCR) technology (Hultman, T., S. Bergh, T. Moks, M. Uhlen [1991] Biotechniques 10:84–93; Landgraf, A., B. Reckmann, A. Pingoud [1991] Analytical Biochemistry 193:231–235; Zimran, A., C. Glass, V. Thorpe, E. Beutler [1989] Nucleic Acids Res. 17:7538) have further expanded the need for convenient and versatile reagents to chemically modify oligonucleotides."

"Current methods to introduce chemical modifications into oligonucleotides typically employ the use of non-nucleosidic phosphoramidite reagents during automated oligonucleotide synthesis. Such methods, however, are generally limited to single modifications at only the 5' terminus, since the 3' terminus remains attached to the solid support. An inherent disadvantage of such methods is that the labeling reagents tend to terminate chain elongation at the point they are introduced (5' terminus) and therefore only single modifications can be performed. Chemical modifications that have been introduced in this fashion are primary aliphatic amine (Sinha, N. D., R. M. Cook [1988] Nucleic Acids Res. 16:2659–2669) and thiol (Connolly, B. [1985] Nucleic Acids Res. 13:4485–4502) functionalities. Oligonucleotides functionalized with primary aliphatic amines or thiol groups must be subsequently derivatized with labels such as biotin, fluorescein, and enzymes. Such derivatization requires a second reaction and purification step which minimizes the convenience and practicality of this method. Cocuzza expanded this method to directly incorporate a single biotin label into an oligonucleotide at the 5' terminus (Cocuzza, A. [1989] Tetrahedron Lett. 30:6287–6290)."

Nelson et al. introduced a new type of non-nucleosidic phosphoramidite reagent that employs a 1,2-ethanediol backbone (Nelson, P., R. Sherman-Gold, R. Leon [1989] Nucleic Acids Res. 17:7179–7186). This reagent allowed primary aliphatic amines to be incorporated multiple times and at any position of the oligonucleotide. The development of this method was said to eliminate the termination of chain elongation during synthesis, an inherent problem of the above method. Employment of the 1,2-ethanediol backbone allowed the phosphoramidite reagent to be incorporated in the same manner as a normal nucleoside phosphoramidite, at any position and multiple times. Misiura et al. expanded the use of the 1,2-ethanediol backbone derived from a glycerol intermediate, to directly incorporate multiple biotin groups into oligonucleotides (Misiura, K., I. Durrant, M. Evans, M. Gait [1990] Nucleic Acids Res. 18:4345–4354). The development of a 1,2-ethanediol backbone modification method was also said to provide better utility and versatility, especially in the field of gene probe diagnostics where multiple labels yield greater signal detection.

A more recent approach, described in U.S. Pat. No. 5,451,463 (Nelson et al.), is said to overcome the above-described disadvantages by providing improved non-nucleosidic reagents to directly modify or label oligonucleotides via automated solid phase synthesis. The '463 patent provides a trifunctional reagent possessing a primary hydroxyl, a secondary hydroxyl, and a primary amino group. This reagent is said to be useful in solid phase oligonucleotide synthesis for the convenient labeling of the 3'-terminus. The secondary hydroxyl may be a phosphoramidite derivative permitting the attachment to the solid phase support. The reporter molecule may be attached to the trifunctional molecule prior to the completion of the oligonucleotide synthesis or after the oligonucleotide is cleaved from the support.

Finally, U.S. Pat. No. 5,723,591 (Livak et al.) describes an oligonucleotide probe which includes a fluorescent reporter molecule and a quencher molecule capable of quenching the fluorescence of the reporter molecule. The oligonucleotide probe is constructed such that the probe exists in at least one single-stranded conformation when unhybridized where the quencher molecule is near enough to the reporter molecule to quench the fluorescence of the reporter molecule. The reporter molecule (e.g., fluorescein dye) is separated from the quencher molecule (e.g., rhodamine dye) by at least about 15 nucleotides, more preferably at least about 18 nucleotides. In one embodiment, the oligonucleotide probe is immobilized on a solid support either directly or by a linker.

What is clearly needed however are reagents adapted to provide further options in the course of oligonucleotide synthesis, such as longer spacers and/or the ability to be used as either the support or as an amidite. Such longer spacers can be used, for instance, to optimize the binding of biotin to avidine, or to reduce steric interference of such labels when double stranded oligonucleotides (one or both of which strands may include such labels) are hybridized to each other.

SUMMARY OF THE INVENTION

The present invention provides a new labeling reagent for use in oligonucleotide ("oligo") synthesis, as well as a method of preparing such a labeling reagent, a method of using such a reagent for synthesizing a labeled oligonucleotide, and an oligonucleotide prepared using such a reagent. Depending on its conditions of preparation and/or use, a reagent of the present invention can be used to label either the 3' or 5' termini of a synthesized oligonucleotide, and/or for one or more positions along the oligonucleotide.

The labeling reagent is preferably prepared as the condensation product of a tritylated hydroxyacid and a diamine, in a manner that provides the resulting linear reagent backbone with one or more label attachment sites and one or more sites for attaching the reagent to a support or amidite. The labeling reagent is more preferably prepared by a reaction scheme that involves the initial preparation of a DMT-hydroxyacid intermediate in the manner provided herein.

The invention therefore provides a labeling reagent useful in making labeled oligonucleotides, the reagent preferably comprising the reaction (e.g., condensation) product of a DMT-hydroxyacid and a diamine, wherein the reaction product provides at least one secondary hydroxyl group. In one particularly preferred embodiment, the hydroxacid itself provides at least one internal amide bond prior to condensation with a diamine. The resulting reagent provides the secondary hydroxyl group residue, either attached to a solid support or converted to a phosphoramidite, and further provides one (primary or secondary) amine group residue having a suitable label or protecting group attached thereto.

In one preferred embodiment, the invention provides a reagent having the following structure selected from:

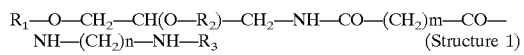
(Structure 1)

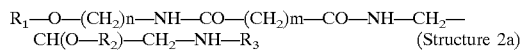
(Structure 2a)

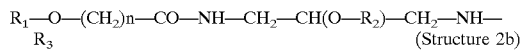
(Structure 2b)

and

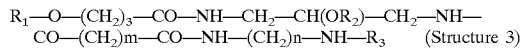
(Structure 3)

wherein:

$R_1$ is 4,4'-dimethoxytrityl ("DMT"), 4-monomethoxytrityl ("MMT") or any other hydroxyl protecting group stable to oligonucleotide synthesis conditions;

$R_2$ is selected from the group consisting of:

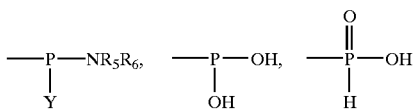

and salts thereof (i.e., phosphorous groups for use in providing coupling reagents), wherein $R_5$ and $R_6$ are independently selected from the group consisting of C3 to C10 branched alkyl, C1 to C12 unbranched alkyl, and cyclic hydrocarbons, and Y is any phosphate protecting group. In a preferred embodiment, $R_5=R_6CH(CH_3)_2$. Optionally, $R_2$ can include a cleavable (under conventional oligonucleotide cleavage conditions) or noncleavable linkage to (and including) a suitable support such as a controlled pore glass (CPG) support, or to (and including) a glass or polymeric support for preparing an oligonucleotide array, or to (and including) an alkylamine CPG support wherein alkyl is 1 to 50 carbon atoms and isomeric forms thereof, or to (and including) a chemically modified CPG, to or (and including) a suitable polymer, such as polystyrene or divinylbenzene;

Also, in structures (1) through (3) above, $R_3$ is a label or reporter molecule (occasionally referred to collectively herein as "label"), which is stable under the conditions of oligonucleotide synthesis, preferably selected from the group consisting of biotin, fluorescein, rhodamine, 4-(4'-Dimethylamino-phenylazo)benzoic acid ("Dabcyl"); 4-(4'-Dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives, ethylenediaminetetraaceticacid ("EDTA"), and derivatives and analogs thereof; as well as radioactive labels;

m=is between 2 and 4, inclusive, and can be selected by the number of methylene groups in the cyclic anhydride used in making the hydroxyacid intermediate; and n=is between 2 and 100, inclusive, and more preferably between 2 and 20, inclusive, and can be selected by the number of methylene groups present in the precursor diamine, hydroxyacid, or aminoalcohol moieties. In case of ethyleneglycol diamines and ethyleneglycol amino alcohols, methylene groups can be replaced by corresponding ether bonds.

The secondary hydroxyl group provided by such a reagent can be used or protected in any suitable fashion. In one preferred embodiment the hydroxyl group is used to attach the reagent to a solid support in order to generate a solid support resin for use in oligonucleotide synthesis. The resulting resin, in turn, can be used to support the synthesis of an oligonucleotide that incorporates a residue of the reagent (including any label attached thereto) at the 3' terminus of the newly synthesized oligonucleotide. In one suitable mechanism, for instance, the hydroxyl group can be succinylated (converted to an ester) by reaction with succinyl anhydride, in order to cleave the anhydride, forming a carboxylic acid group. The carboxylic acid, in turn, can be coupled to a group such as an amine group provide by a support such as CPG, in order to form an amide linkage between the reagent and support. The resulting support can be used as a 3' labeling reagent in solid phase oligonucleotide synthesis.

Alternatively, the hydroxyl group can be converted to a phosphorylating group, in order to permit the resultant reagent to be used in solution and in the course of oligonucleotide synthesis for 5' and internal labeling. Preferred phosphorylating groups include phosphoramidite groups, and particularly, cyanoethylphosphoramidite groups.

A labeled phosphoramidite of this invention, and particularly those having long spacers, can be used for attaching a label at the 3'-end of an oligonucleotide in a manner that is sufficiently stable towards regular cleavage conditions typically used in the deprotection and/or cleavage of oligonucleotides. Such stable linkages can be obtained, for instance, when an aminated support is converted to a hydroxylated support, which upon reaction with the amidite reagent of this invention forms the phosphite bond. The phosphite bond, in turn, is typically oxidized to a phosphotriester and upon deprotection steps is converted to a stable phosphodiester. The provision of a hydroxylated support, or conversion of an aminated support to a hydroxylated support, can be accomplished by any suitable means, e.g., by treating an aminated support with gamma-butyrolactone under conditions (e.g., heating) suitable to convert the amine functionalities to corresponding 3-hydroxypropyamido functionalities. Such a process can be performed using aminated supports such as aminopropyl-CPG or long chain alkylamine-CPG (LCAA-CPG) supports that are commercially available, as well as aminated polystyrene supports.

Given the present description, those skilled in the appropriate art will be able to employ a variety of suitable synthetic strategies for such purposes, e.g., as described in Vu, et al., *Nucleosides and Nucleotides* 12(8):853–864 (1993), the disclosure of which is incorporated herein by reference. A DMT-hydroxyacid intermediate can be prepared in a reaction between an aminoalcohol and a cyclic anhydride, typically succinic anhydride. To the extent any such hydroxyacids are not commercially available, they can be prepared in the manner described herein.

An amine group, for use as the $R_3$ substituent in a reagent of the present invention, can itself be functionalized with a variety of labels, e.g., selected from the group consisting of biotin, fluorescein, rhodamine, 4-(4'-dimethylaminophenylazo)benzoic acid ("Dabcyl"); 4-(4'-dimethylaminophenylaz acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof; and radioactive labels. The labeling reagents of this invention can include succinylated labeling reagents (and other ester derivatives), e.g., in a form coupled to a support for 3'-end labeling, or in the form of a phosphoramidite labeling reagent for 5'-end labeling or for internal labeling of an oligonucleotide.

The labeling reagents described herein can be prepared using materials that are commercially available or that can be readily synthesized, given the present description. In turn, the extent of spacing providing by a reagent can be varied as desired, e.g., by the selection and use of a wide variety of diamines that are commercially available and inexpensive (e.g., as used in the production of Nylon).

DETAILED DESCRIPTION

Preparation of DMT-Hydroxyacids and Condensation with Diamines

Hydroxyacids that are generally not available can be prepared on a case by case basis, e.g., a suitable aminoalcohol can be readily reacted with a cyclic anhydride to form an amide bond. In order to prevent ester bond formation to the available hydroxyl groups, the reaction mixture can typically be heated for 1–2 days at 60 degree Celcius in the presence of equimolar amounts of diisopropylethylamine in pyridine or pyridine dimethylformamide solution. Upon completion, 1/10 equivalent of dimethylaminopyridine can be added to catalyze the tritylation of the primary hydroxyl group with one equivalent of DMT-Cl. The reaction can be allowed to proceed for 3 days at room temperature.

The solvents are then removed and the product is typically extracted with a suitable ethylacetate/water mixture having a pH of about 5 in order to protonate the acid. The degree of detritylation is minimal but pyridine should be added should the solution be evaporated. The activation of the carboxylic group for coupling to a diamine can be accomplished by conventional procedures such as dicyclohexylcarbodiimide in the presence of N-hydroxy succinimide or N-hydroxybenzotriazole. The amine is typically dissolved in DMF (dimethylformamide) and the activated DMT-hydroxyacid added. The condensation is instantaneous at room temperature and after about 2 hours the solvent is evaporated and the product taken up in an organic solvent typically ethyl acetate or dichloromethane.

A label can then be attached to the amine group of the reagent backbone, having $R_1$ (here, DMT) already in place, typically by the formation of an amide linkage after activation of the label's own carboxylic group. Depending on the use of the labeling reagent, either 1) the hydroxyl group can be succinylated in pyridine using established methods in the field for subsequent attachment to an aminated solid support typically controlled pore glass or polystyrene, or 2) the labeling reagent can be used in solution for 5' labeling. The secondary hydroxyl group of the labeling reagent can then be converted to an activated phosphorylating reagent, typically a phosphoramidite, and preferably a cyanoethylphosphoramidite.

Synthesis of DMT-Hydroxyacid: A suitable hydroxyacid can be generated in a reaction between an aminoalcohol and a cyclic anhydride, typically succinic anhydride. Generally such hydroxyacids are not commercially available, but instead are prepared in the manner provided herein. For instance, when 1,2-dihydroxy-3-aminopropane is used in such a reaction the following hydroxyacid is obtained:

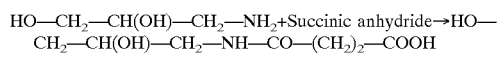

Tritylation with DMT-Cl (dimethoxytrityl chloride): The resulting hydoxyacid can then be tritylated, preferably under conditions that provide tritylation of the primary (as opposed to secondary) hydroxyl group, to provide a DMT-hydroxyacid having the secondary hydroxyl group free as depicted below:

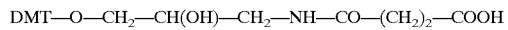

The carboxylic group of the resulting DMT-hydroxyacid can be activated to an active ester of N-hydroxybenzotriazole using dicyclo hexylcarbodiimide. The resulting intermediate can then be condensed with excess diamine to generate another amide bond. The product thus obtained is extractable in organic solvents giving the label reagent as depicted below:

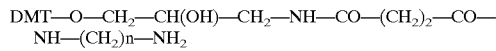

wherein the n=the number of methylene groups in the diamine, or when polyethyleneglycol diamines are used, some methylene groups are replaced by corresponding ether groups.

The general formula of the resulting compound is analogous to Structure (1) above, where $R_1$ is now a protecting group for the primary hydroxyl group, $R_2$ is H, but can be adapted to provide the attachment of the secondary hydroxyl group to a support or conversion to an amidite, $R_3$ is H, but can be adapted to include a label attached to the amine group, n is the number of methylene groups in the diamine used for making the precursor labeling reagent, and m is 2.

The backbone of the labeling reagent thus synthesized can now be labeled via its amine group, commonly through an activated carboxylic group of the label, with the formation of an amide linkage between the label and backbone above. Succinylation or similar esterfications at the hydroxyl can be used to generate a free carboxylic group, that in turn, can be attached to aminated support, again through an amide bond. The secondary hydroxyl group can also be converted to a phosphoryalting reagent such as a phosphoramidite for coupling to the 5'-end of an oligonucleotide or within the oligonucleotide sequence.

Representative diamines suitable for use in the method of this invention include those having primary and/or secondary amine groups, examples of which include: ethylenediamine, hexamethylenediamine, diaminocyclohexanes, 1,12-diaminododecane, 1,7-diaminoheptane, 1,6-diaminohexane, 1,8-diamino-p- menthane, 1,5-diaminopentane, 1,3-diaminopropane, poly(propyleneglycol)-block-poly(ethyleneglycol)-block-poly(propyleneglycol)bis(2-aminopropyl) ether, 1,3-bis(aminomethyl)cyclohexane, 1,4-bis(3-aminopropyl)piperazine, N,N'-bis(3-aminopropyl)1,3-propanediamine, 1,3-diamino-2-propanol, 2,2'-(ethylenedioxy)bis(ethylamine), 1,4-diaminobutane, 2,4-diaminobutyric acid, lysine, 4,7,10-trioxa-1,13-trand 4,9-dioxa-1,12-dodecanediamine.

Those skilled in the art will appreciate the manner in which the spacer characteristics (e.g., length) can be varied to optimize the labeling reagents, from both a chemical as well as economical point of view. The above list of diamines, and the corresponding spacers they provide, are typically commercially available and inexpensive, which further demonstrates the potential benefits of the present invention.

A reagent of this invention can be provided by the reaction of an available amine group, as provided by the use of a diamine, and can be used as is, or can itself be functionalized with a variety of labels as described herein, e.g., biotin, fluorescien, acridine, tetramethylrhodamine, and dabsyl, as well as other reagents used or useful in the course of oligonucleotide synthesis or related applications. An available hydroxyl group, as provided by the use of an alcohol moiety, can be used as is, or can itself be used to attach the reagent to a support, e.g., to a solid support. Alternatively, the hydroxyl can be converted to a phosphorylating reagent and the resulting reagent can be used as a solution phase reagent in order to couple the reagent to a growing oligonucleotide sequence. Preferred phosphorylating reagents include phosphoramidites and particularly cyanoethylphosphoramidites.

Reagents of the subject invention are useful in oligonucleotide synthesis (both oligodeoxyribonucleotide and oligonucleotide) to chemically modify a synthetic oligonucleotide at any position with any chemical functional group. Reagents wherein $R_2$ includes CPG (or a modified CPG) are useful for modifications at the 3' terminus. Reagents wherein $R_2$ does not include a support such as CPG are useful for modifications at the 5' terminus or at internal locations.

A reagent of the present invention can be used to directly label an oligonucleotide. Also, the reagent can be used for attaching a label to a functional group introduced at any position of a synthetic oligonucleotide. This "indirect" labeling of the functional group can be accomplished, for instance, by using a reagent of the subject invention having a protected functional group. Amino-modifiers can be used for post synthesis labeling, wherein an amine protecting group is removed and the amine itself reacted with an active ester of the label. Fluorescein active esters, TAMRA active esters, biotin active esters are commonly used.

For instance, a functional amine can be protected by compounds such as 9-fluorenylmethoxycarbonyl ("FMOC"), monomethoxytrityl, or trifluoroacetyl ("TFA") protecting groups. Such a protected amine, when used in oligonucleotide synthesis, provides an amino-modifier adapted to permit a label or other group to be incorporated post-synthesis. (see Glen Research Catalog page 33, 1999). When used in connection with labeling of oligonucleotides, the protecting group on the amine can itself be removed after the completion of synthesis, using a mild anhydrous base such as piperedine, thereby exposing the reactive amine. An active ester is then commonly coupled to the amine group in a post-synthesis reaction, in order to incorporate the label. For instance, the N-hydroxysuccinimide ester of biotin, can also be used for post-synthesis labeling using reagents having an amino modifier function as described herein. As with unmodified reagents, the amino-modifier reagent can also be attached to the support in order to put a label at the 3'-end or it can be in the form of a phosphoramidite for 5'-end labeling or post-synthesis internal labeling.

In a manner analogous to the reagents of the above-cited Nelson ('463 patent), the reagents and methods of the present invention can be used to introduce functional groups and labels at multiple sites of a nucleotide during oligonucleotide synthesis. Such modified and labeled oligonucleotide probes can be used in any application where the probe hybridizes to complementary sequences of a target polynucleotide. Further, primers made from the reagents of the subject invention can be used in the polymerase chain reaction (PCR) to amplify the target gene segment and then employing the invention for detecting the presence of specific polynucleotide in samples containing the same, biological samples, and, for example, clinical samples such as serum and blood. Still further, the method and reagents of this invention can be used for the diagnosis of infectious diseases and pathogens, detection of oncogenes, diagnosis of genetic disorders, and detection of point mutations or single base substitutions.

Examples of suitable labels and reporter molecules include, but are not limited to:

Biotin;

Fluoresceins (including derivatives and analogs thereof), such as the following:
- 5-carboxyfluorescein
- 6-carboxyfluorescein
- 5-(and 6)carboxy-2',7'-dichloro-fluorescein
- 5-(and 6)2',4',5',7',-tetrachlorofluorescein
- 5-(and 6-)carboxy-4,7-dichloro-2',7',-dimethoxyfluorescein
- 5-(and 6-)carboxy-4,7-dichloro-fluorescein
- 5-(and 6-)carboxy-4,7,4',5',-tetrachloro-fluorescein
- 5-(and 6-)carboxy-4',5'-dichloro-2',7'-dimethoxyfluorescein
- 5-(and 6-)carboxy-4,7-dichloro-1',2',7',8'-dibenzofluorescein
- 5-(and 6-)carboxy-4,7,4',5'-tetrachloro-1',2',7',8'-dibenzofluorescein
- 5-(and 6-)carboxy-4,7,4',5'-tetrachloro-2',7'-dimethoxyfluorescein
- 5-(and 6-)aminomethylfluorescein
- 4',5'-dimethoxy-5(and 6-)carboxyfluorescein (commercially available from Molecular Probes, Inc. Eugene, Oreg., and Lee et al., see also, Nucleic acids Research Vol 20, No 10, 2471–2483 (1992), the disclosure of which is incorporated herein by reference. Commercial examples of fluorescien/rhodamine including Bodipy and bifluoresceins such as BODIPY-Fluorescein analog, Tetramethylrhodamine analog, Texas Red analog);

Rhodamines (including derivatives and analogs thereof) such as
- 5-(and 6-)carboxyrhodamine
- 5-(and -6)carboxytetramethylrhodamine ("TAMRA")
- Rhodamine Red
- Rhodamine Green;

4-(4'-Dimethylamino-phenylazo)benzoic acid ("Dabcyl");

4-(4'-Dimethylamino-phenylazo)sulfonic acid (sulfonyl chloride) ("Dabsyl");

5-((2-aminoethyl)-amino)-naphtalene-1-sulfonic acid ("EDANS");
Psoralene derivatives such as:
8-methoxypsoralene
4,5',8-trimethylpsoralene
(see, e.g., Isaacs, et al., Biochemistry Vol 16, No 6. 1058–1064 (1977));
Haptens, such as 2,4-dinitro-phenyl-;
Cyanines (e.g., those available under the trademarks Cy3TM and Cy5TM of Amersham Pharmacia); as well as cyanine dye labeling reagents, sulfoindocyanine succinimide esters (see Mujumdar et al., Bioconjugate Chemistry Vol 4, No 2. 105–112 (1993) incorporated herein by reference);
Acridines such as 2-Methoxy-6-chloro-9-aminoacridine derivatives (see Asseline et al., Bioconjugate Chemistry Vol7, No 3. 369–378 (1996) incorporated herein by reference);
Fluorescent Rhodol derivatives such as 5-(and 6-)carboxy-2',7'-dimetyl-3'-hydroxy-6'-ethylaminospiro (isobenzofuran-1(3H),9-(9H)xanthen)-3-one (see Whitaker et al. Analytical Biochemistry Vol 207 267–279 (1992) incorporated herein by reference);
Cholesterol derivatives;
Ethylenediaminetetraaceticacid ("EDTA") and derivatives thereof;
and radioactive labels attached to the labeling reagents of this invention, including but not limited to, $P^{32}$, tritium, and $I^{125}$.

The present invention also has utility in the areas of anti-sense molecular biology, electron microscopy, X-ray crystallography, and site-specific cleavage of DNA. The reagents and resultant oligos of this invention can also be used in DNA sequencing using procedures well known to those skilled in the art. See, for instance, the following references: Hultman, T., S. Bergh, T. Moks, M. Uhlen [1991] BioTechniques 10:84–93), chemiluminescent sequencing (Martin, C., L. Bresnick, R. R. Juo, J. C. Voyta, I. Bronstein [1991] BioTechniques 11:110–113), and quantitative analysis (Landgraf, A., B. Reckmann, A. Pingoud [1991] Anal. Biochem. 193:231–235), the disclosures of which are incorporated herein by reference.

The present synthetic approach provides a rapid method for preparing labeling reagents. It permits the use of simple, commercially available starting materials. The tritylated starting material can be isolated in high yield and pure form. Selective tritylation need not be performed later, as in other approaches, which require expensive and tedious separation by chromatography.

The methodology can employ common diamines for building the spacer attachment. A number of diamines are available at very low price since many are used in Nylon manufacturing. Hexamethylenediamine can be used, for instance, to provide a spacer that is 15 atoms long and 4,7,10-trioxa-1,13-tridecanediamine, a spacer of 22 atoms long, for example. As a comparison, the Nelson '463 patent provides a laborious scheme for obtaining its reagent identified as "compound 2". Since selective tritylation is not possible (where there are two equal hydroxyl groups), the Nelson reference instead relies on purification by chromatography. Nelson also relies on the availability of a 4-bromo-butyronitrile as a starting material followed by several steps to prepare compound 2. As Nelson itself points out, the ability to control the length of the spacer can be crucial for some interactions, such as the binding of biotin to avidin.

A conventional biotin labeling reagent on the market today is biotin-TEG phosphoramidite (available from Glen Research as product #10-1955-02). This product currently sells for about $2,700 per gram and provide a spacer of 16 atoms. Using the method of the present invention, a comparable biotin labeling reagent can be prepared for less than $50 per gram. As described above, the reagent of this invention can also be combined with, and used for, solid phase CPG (controlled pore glass) synthesis. By replacing the phosphoramidite group with a CPG group, direct 3' modification can be achieved.

The present synthesis strategy differs from previously disclosed methods in a variety of ways, including the fact that the labeling reagents, for use in either solution (as amidites) or on a labeled support (3'-labeling), are obtained by a streamlined method, having fewer chemical steps. This, in turn, can translate into a more cost-effective manufacture of those expensive labeling reagents used in the field. One of the more striking differences in the present, preferred, synthesis protocol, is that the starting reagent can itself be provided with a protective trityl group. This can be important in several ways. First, it means that the starting material can be easily obtained in a very pure form, since the DMT-hydroxyacids can be easily purified by extraction. Second, the ability to include the DMT group from the beginning, obviates the more conventional need for a tritylation step later in the synthetic process, e.g., at a point after the labels themselves have been attached. This becomes particularly important when labeling reagents are themselves able to be tritylated, such as biotin.

Moreover, the synthesis strategy of this disclosure can rely on purification of intermediates by extraction instead of chromatography, as used in most other methods. The desired labeling reagent precursor, in turn, can be readily extracted in the organic phase and in considerable yield and purity.

The reagent of general structure 2(a) can be prepared using DMT-hydroxyacids that are themselves prepared from aminoalcohols such as 2-aminoethanol or 6-aminohexanol, by succinylation and tritylation. In these examples the DMT-derivative does not have an hydroxyl group as before. In order to build a labeling reagent with the necessary functions for a labeling reagent of the kind previously disclosed, it is desired to add the amine function and a hydroxyl function for the reasons already discussed. This can be accomplished by the condensation of such DMT-hydroxyacids with 1,3-diamino-2-propanol. The synthesis can thus be describes as depicted below:

An amino-mono-alcohol, such as 2-aminoethanol or 6-aminohexanol, is first succinylated and then tritylated as described previously:

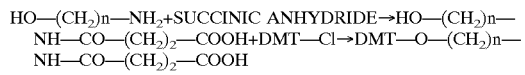

The resulting DMT-hydroxyacid can be isolated or can be directly coupled to 1,3-diamino-2-propanol following the procedure in the Example below. The resultant product is depicted below:

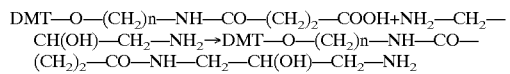

In which case, n=the number of methylene groups in the aminoalcohol, or when ethylene glycol aminoalcohols are used, one or more methylene groups are replaced by one or more ether groups.

The general formula of the labeling reagent of these reactions above, is shown in the Summary of the Invention,

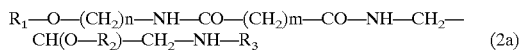
(2a)

where the various R groups, and values for m and n, are as provided herein.

The amine group is used for the attachment of labels typically through an amide bond, or protecting groups such as FMOC when used as aminolinker. The hydroxyl group is attached to a solid support typically through a cleavable succinyl ester linkage. Such construct is thus used for labeling reagent for the 3' end of an oligonucleotide or as a solid support. The hydroxyl group can also be converted to phosphorylating group, e.g., phosphoramidite and used for the internal of 5' labeling of an oligonucleotide.

A labeling reagent of general structure (2b) can be obtained by a reaction scheme similar to that described with respect to Structure (2a), e.g., in which commercially available 12-hydroxydodecanoic acid (HO—(CH$_2$)$_{11}$—COOH) is used instead of the prepared hydroxyacids as disclosed above.

The 12-hydroxydodecanoic acid is tritylated with DMT-Cl and then coupled to 1,3-diamino-2-propanol to give the labeling reagent precursor below:

DMT—O—(CH$_2$)$_{11}$—CO—NH—CH$_2$—CH(OH)—CH$_2$—NH$_2$

This precursor can be used in the manner provided herein to provide a labeling reagent of Structure (2b), as shown below and in the Summary of the Invention:

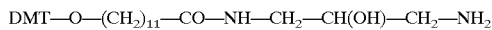

A reagent of general structure (3) above can be prepared using yet another DMT-hydroxyacid, e.g., made from a 1,3-diamino-2-propanol derivative, which is then condensed with a diamine in order to provide another backbone that is somewhat different from the backbones of Structures (1) and (2a) or (2b). The reaction of 1,3-diamino-2-propanol in excess, with gamma-butyrolactone upon heating at 60° C. for 2 hours yields mainly the 1-hydroxypropyl-amido-3-amino-2-propanol below, plus unreacted 1,3-diamino-2-propanol:

Gamma-butyrolactone+1,3-diamino-2-propanol→HO—(CH$_2$)$_3$—CO—NH—CH$_2$—CH(OH)—CH$_2$—NH$_2$ The available amine groups, including those of the unreacted staring material, are then treated with equivalent amount of succinic anhydride as described herein, in order to convert them to succinylamides and provide a final product that can be easily and efficiently isolated. Once the succinylation is complete, in the manner described herein, the primary hydroxyl group can be tritylated with one equivalent of DMT-Cl. The DMT-hydroxyacid obtained, is the only reaction product that is extractable in dichloromethane or ethyl acetate, since any other products will tend to be too hydrophilic to be taken up in these solvents.

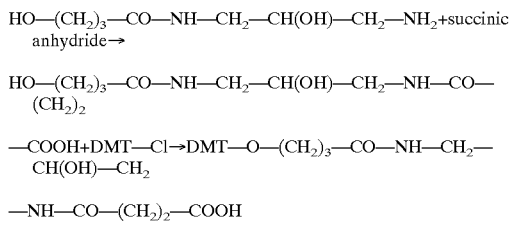

The DMT-hydroxyacid is activated and reacted with a diamine NH$_2$—(CH$_2$)n—NH$_2$ as described herein, providing the following backbone molecule.

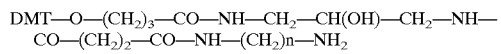

In turn, the general formula of the labeling reagent is given in the Summary of the Invention,

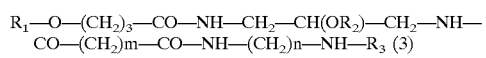
(3)

where the various R groups, and values for m and n, are as provided herein.

Preparation and Use of DMT-hydroxyacids as Spacers

The DMT-hydroxyacids described herein, and derivatives thereof, can themselves be used as spacers in combination with labeling reagents such as those presently described. The preparation and use of hydroxyacids in this manner is considered novel in its own right. By reference to U.S. Pat. No. 5,723,591, the complete disclosure of which is incorporated herein by reference, the use of long spacer attachments to solid supports is preferred when dual labeled probes are used in oligonucleotide detection systems. The spacers used in the '591 patent, however, have a distribution range of 400 to 4600 daltons. Such a range of spacers may, however, generate different hybridization kinetics, as compared to a population of spacers having the same or similar lengths. By the selection and use of DMT-hydroxyacid spacer of this disclosure, we can construct spacers of defined, controllable and uniform lengths.

A DMT-hydroxyacid prepared, for instance, from 6-aminohexanol and succinic anhydride and DMT-Cl, can find use as a spacer in many forms. Spacing can be controlled and defined by the number of atoms in the chain between reactive sites in the molecule, in this case between the DMT-group and the OH of the carboxylic acid. The following structure, for instance, provides a 12 atom spacer.

DMT—O—(CH$_2$)$_6$—NH—CO—(CH$_2$)$_2$—COOH

This 12 atom spacer, when condensed to an aminated support through an amide bond, can be used to generate a 12 atom non-cleavable spacer that is stable towards standard ammonium hydroxide deprotection (55° C. for 12 hours). A phosphoramidite can also be attached, e.g., after detritylation of the spacer using regular DNA synthesis chemistry. The resulting process can be used to generate dual label probes, for example, that are immobilized on a support, using the labeling reagent of this invention.

When reacting or condensing the 12 atom spacer above, with 4,7,10-Trioxa-1,13-tridecanediamine, the resultant product would have a spacer arrangement of 27 atoms as depicted below.

DMT—O—(CH$_2$)$_6$—NH—CO—(CH$_2$)$_2$—CO—NH—(CH$_2$)$_3$—O—(CH$_2$)$_2$—O—(CH$_2$)$_2$—O—(CH$_2$)$_3$—NH$_2$

If the molecule is succinylated, and coupled to an aminated support as described for the 12 atom spacer above, it is possible to provide a spacer that is 31 atoms in length. Again, if increased spacing is desirable this construct can be used.

In yet another application, the 12 atom spacer above can be condensed with an aminoalcohol such as 6-aminohexanol, to provide the 20 atom spacer depicted below.

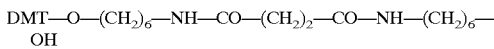

Upon conversion of the terminal hydroxyl group to an amidite, $R_3$, such a spacer could be repeatedly reacted as an amidite and detritylated, generating one multiple per coupling reaction, in order to provide a defined length and a non-cleavable spacer to a hydroxylated solid support or array. For instance, five repeated coupling reactions of DMT—O—(CH$_2$)$_6$—NH—CO—(CH$_2$)$_2$—CO—NH—(CH$_2$)$_6$—O—R$_3$ would generate a spacer of 100 atoms with an approximate molecular weight of 2000 daltons.

It is understood that various precursors described herein can exist, and may be obtained, as various optical isomers. Those skilled in the art, given the present description, will appreciate the manner in which various optical isomers, or racemic mixtures thereof, can be used in the synthetic method of this invention. de

EXAMPLE

Preparation DMT-Hydroxyacids and Condensation to Diamines ("One Pot Synthesis" of Labeling Reagent)

3-Amino-1,2-propanediol (0.1 mol) is dissolved in DMF (30 ml) and pyridine (20 ml) and diisopropylethyl amine (0.1 mol) in a round bottom flask with stopper. Solid succinic anhydride (0.1 mol) is added under stirring at room temperature. After 30 minutes the mixture is transferred to an oven at 60° C. and kept for two days. The mixture is cooled to room temperature and dimethylaminopyridine (0.01 mol) is added followed by solid DMT-Cl (0.1 mol). The mixture is stirred at room temperature for 2 days. The free carboxylic group in the crude mixture is activated by HOBt (0.1 mol) in the presence of an additional amount of diisopropylethylamine (0.2 mol) for 5 minutes, and then added to a solution of hexamethylenediamine (0.5 mol) in DMF (75 ml). The reaction is kept at room temperature for 2 hours. The excess solvent mixture is evaporated at reduced pressure. The residue is taken up in ethyl acetate (200 ml) and the organic phase is washed with water and brine. The organic phase is dried and evaporated to an oil and then taken up in DMF (20 ml) to be used as a stock solution when attaching labels to aliquots thereof. 2 ml of the stock solution corresponding to 10 mmol if theoretical yield is added to a solution of 4-(4'-Dimethylamino-phenylazo)benzoic acid ("Dabcyl")-N-hydroxy succinimide ester (8 mmol) in DMF (25 ml).

The mixture is stirred for 2 hours at room temperature. The solvent is evaporated and the product extracted with dichloromethane, water, phosphate buffer pH 6 and brine. The Dabcyl labeled product can be passed through a silica column using dichloromethane 10% methanol as eluent or used directly for succinylation. The labeling reagent is coupled to LCAA (Long Chain Alkyl Amine controlled pore glass, 500A) at a loading of 30 to 50 micromole per gram. The reagent is used as a quencher in Molecular Beacons®.

What is claimed is:

1. A method of preparing a labeling reagent for use in oligonucleotide synthesis, the method comprising the steps of providing a tritylated hydroxyacid and a diamine, and condensing the hydroxyacid and diamine under conditions suitable to provide a reagent backbone having one or more label attachment sites and one or more sites for attaching the reagent to a support or amidite.

2. A method according to claim 1 wherein the tritylated hydroxyacid comprises a DMT-hydroxyacid.

3. A method according to claim 1 wherein the method is used to prepare a reagent selected from the group:

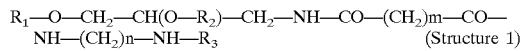

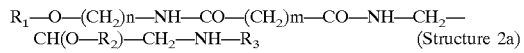

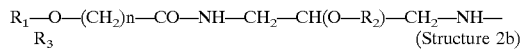

and

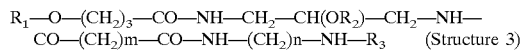

wherein:

$R_1$ is 4,4'-dimethoxytrityl, 4-monomethoxytrityl or any other hydroxyl protecting group stable to oligonucleotide synthesis conditions;

$R_2$ is either selected from the group consisting of:

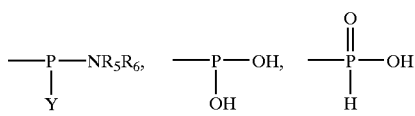

and salts thereof, wherein $R_5$ and $R_6$ are independently selected from the group consisting of C3 to C10 branched alkyl, C1 to C12 unbranched alkyl, and cyclic hydrocarbons, and Y is any phosphate protecting group, or $R_2$ includes a cleavable or noncleavable linkage to (and including) a support material;

$R_3$ is a label or reporter molecule;

m is between 2 and 4, inclusive; and n is between 2 and 100, inclusive.

4. A method according to claim 3 wherein $R_3$ is a label or reporter molecule which is stable under the conditions of oligonucleotide synthesis.

5. A method according to claim 4 wherein the label or reporter molecule is selected from the group consisting of biotin, fluorescein, rhodamine, 4-(4'-Dimethylamino-phenylazo)benzoic acid ("Dabcyl"); 4-(4'-Dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives, ethylenediaminetetraaceticacid ("EDTA"), and derivatives and analogs thereof; as well as radioactive labels.

6. A method according to claim 1 wherein the reagent is attached to a support material by means of a cleavable linkage.

7. A method according to claim 6 wherein the cleavable linkage comprises a succinyl ester linkage.

8. A method of synthesizing an oligonucleotide, comprising the steps of providing a reagent prepared according to the method of claim 1 wherein the reagent is provided in the form of a labeled support and the label is incorporated at the 3' terminus of the oligonucleotide.

9. A method according to claim 8 wherein the reagent is provided in the form of a labeled phosphoramidite reagent and incorporated at either the 5' terminus or along the length of the oligonucleotide.

10. A method according to claim 9 wherein a plurality of reagents are used to provide a corresponding plurality of labels in a single oligonucleotide.

11. A method according to claim 5 wherein
the fluoresceins are selected from the group consisting of;
5-carboxyfluorescein,
6-carboxyfluorescein,
5-(and 6)carboxy-2',7'-dichloro-fluorescein,
5-(and 6)2',4',5',7',-tetrachlorofluorescein,
5-(and 6-)carboxy-4,7-dichloro-2',7',-dimethoxyfluorescein,
5-(and 6-)carboxy-4,7-dichloro-fluorescein,
5-(and 6-)carboxy-4,7,4',5',-tetrachloro-fluorescein,
5-(and 6-)carboxy-4',5'-dichloro-2',7'-dimethoxyfluorescein,
5-(and 6-)carboxy-4,7-dichloro-1',2',7',8'-dibenzofluorescein,
5-(and 6-)carboxy-4,7,4',5'-tetrachloro-1',2',7',8'-dibenzofluorescein,
5-(and 6-)carboxy-4,7,4',5'-tetrachloro-2',7'-dimethoxyfluorescein,
5-(and 6-)aminomethylfluorescein, and
4',5'-dimethoxy-5(and 6-)carboxyfluorescein;
the rhodamines are selected from the group consisting of
5-(and 6-)carboxyrhodamine,
5-(and -6)carboxytetramethylrhodamine ("TAMRA"),
Rhodamine Red, and
Rhodamine Green,
the psoralene derivatives are selected from the group consisting of
8-methoxypsoralene, and
4,5',8-trimethylpsoralene, and
the fluorescent rhodol derivatives comprise 5-(and 6-)carboxy-2',7'-dimetyl-3'-hydroxy-6'-ethylaminospiro(isobenzofuran-1(3H), 9-(9)xanthen)-3-one.

12. A method according to claim 3 wherein $R_3$ is an amine protecting group selected from the group consisting of 9-fluorenylmethoxycarbonyl, monomethoxytrityl, and trifluoracetyl protecting groups, the protecting group being adapted to permit a label or other group to be incorporated post-synthesis.

13. A reagent for use in oligonucleotide synthesis, the reagent comprising a tritylated hydroxyacid of the formula

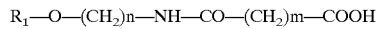

wherein $R_1$ is 4,4'-dimethoxytrityl, 4-monomethoxytrityl or any other hydroxyl protecting group stable to oligonucleotide synthesis conditions; m is between 2 and 4, inclusive; and n is between 2 and 100, inclusive.

14. A method of oligonucleotide synthesis, comprising the steps of providing the reagent of claim 13, condensing the reagent to an aminated support via formation of an amide linkage between the carboxyl group of the reagent and an amine group of the support, and attaching a phosphoramidite in the course of detritylating the reagent.

* * * * *